(12) United States Patent
Venturini et al.

(10) Patent No.: US 8,852,252 B2
(45) Date of Patent: Oct. 7, 2014

(54) ENDOSSEOUS SCREWS AND ORTHOPAEDIC DEVICE TO ASSIST THE RIGID OSTEOSYNTHESIS OF FRACTURES

(75) Inventors: Daniele Venturini, Povegliano Veronese (IT); Giancarlo Marazzi, Milan (IT)

(73) Assignee: Orthofix S.r.l. (IT)

( * ) Notice: Subject to any disclaimer, the term of this patent is extended or adjusted under 35 U.S.C. 154(b) by 153 days.

(21) Appl. No.: 13/058,307

(22) PCT Filed: Dec. 22, 2009

(86) PCT No.: PCT/IB2009/007856
§ 371 (c)(1),
(2), (4) Date: Feb. 9, 2011

(87) PCT Pub. No.: WO2010/073103
PCT Pub. Date: Jul. 1, 2010

(65) Prior Publication Data
US 2011/0245882 A1  Oct. 6, 2011

(30) Foreign Application Priority Data
Dec. 23, 2008 (IT) .............................. BO2008A0769

(51) Int. Cl.
*A61B 17/80* (2006.01)
*A61B 17/86* (2006.01)
*A61B 19/00* (2006.01)
*A61B 17/88* (2006.01)

(52) U.S. Cl.
CPC ......... *A61B 17/8052* (2013.01); *A61B 17/8635* (2013.01); *A61B 17/861* (2013.01); *A61B 2019/307* (2013.01); *A61B 17/8605* (2013.01); *A61B 17/8875* (2013.01)

USPC ........... 606/305; 606/308; 606/319; 411/386; 411/5

(58) Field of Classification Search
USPC ........ 606/280–331, 104, 99, 70–71; 411/423, 411/386, 5, 410
See application file for complete search history.

(56) References Cited

U.S. PATENT DOCUMENTS

| | | | | |
|---|---|---|---|---|
| 2,353,531 | A | * | 7/1944 | Whitney ........................ 411/410 |
| 3,396,765 | A | * | 8/1968 | Ridenour ......................... 81/437 |
| 5,108,399 | A | * | 4/1992 | Eitenmuller et al. ........... 606/77 |
| 5,797,918 | A |   | 8/1998 | McGuire et al. |
| 6,059,786 | A | * | 5/2000 | Jackson ......................... 606/916 |
| 6,398,786 | B1 | * | 6/2002 | Sesic .............................. 606/308 |
| 6,730,091 | B1 | * | 5/2004 | Pfefferle et al. ................. 606/70 |
| 6,969,390 | B2 | * | 11/2005 | Michelson .................. 606/86 B |

(Continued)

*Primary Examiner* — Todd Manahan
*Assistant Examiner* — Jessica Weiss
(74) *Attorney, Agent, or Firm* — Akerman LLP

(57) ABSTRACT

Endosseous screw (1) for fixing a plate (102) to a bone site (300), comprising an at least partially threaded shaft (2), insertion means for inserting the screw into a bone site and a distal portion (33) provided for engaging said plate to fasten it to said bone site and comprising a head (3) having facets (30) defining an external peripheral profile provided for engagement with a tubular manipulating wrench, to allow the screw (1) to be extracted from the bone site (300) into which it has been inserted, wherein the facets (30) are curvilinear and the external peripheral profile defined by same facets (30) has a convex barrel-like shape, in order to allow a stable coupling between the tubular manipulating wrench and said profile, which is maintained during the untightening phase of screw from plate, even when said tubular manipulating wrench is oriented in an inclined direction with respect to a longitudinal axis (x) of the endosseous screw (1).

10 Claims, 3 Drawing Sheets

(56) References Cited

U.S. PATENT DOCUMENTS

| | | |
|---|---|---|
| 2002/0017170 A1 | 2/2002 | Amis |
| 2006/0058796 A1 | 3/2006 | Hartdegen et al. |
| 2006/0081553 A1* | 4/2006 | Patterson et al. ............. 215/252 |
| 2007/0227314 A1* | 10/2007 | Erickson et al. ................ 81/467 |
| 2009/0210014 A1* | 8/2009 | Ziolo et al. .................... 606/286 |

* cited by examiner

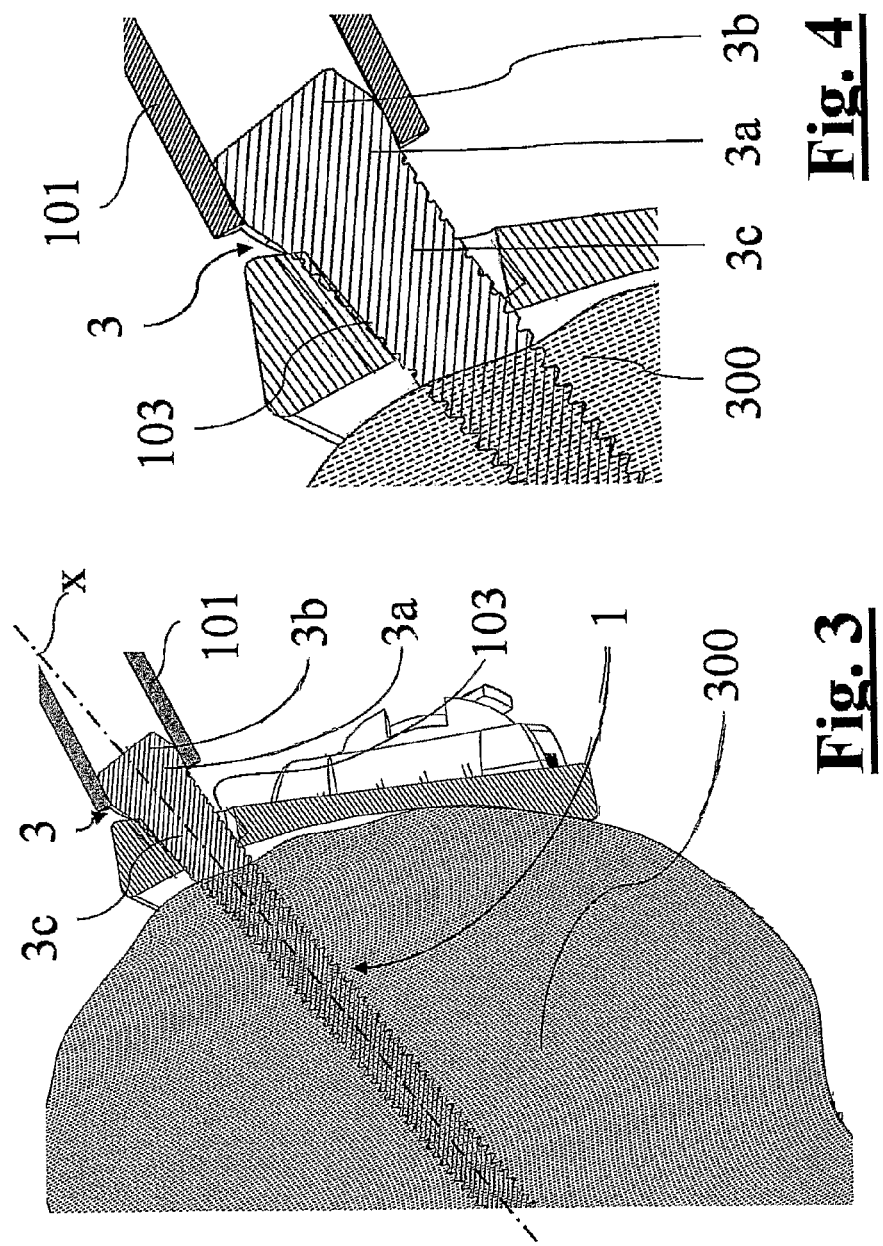

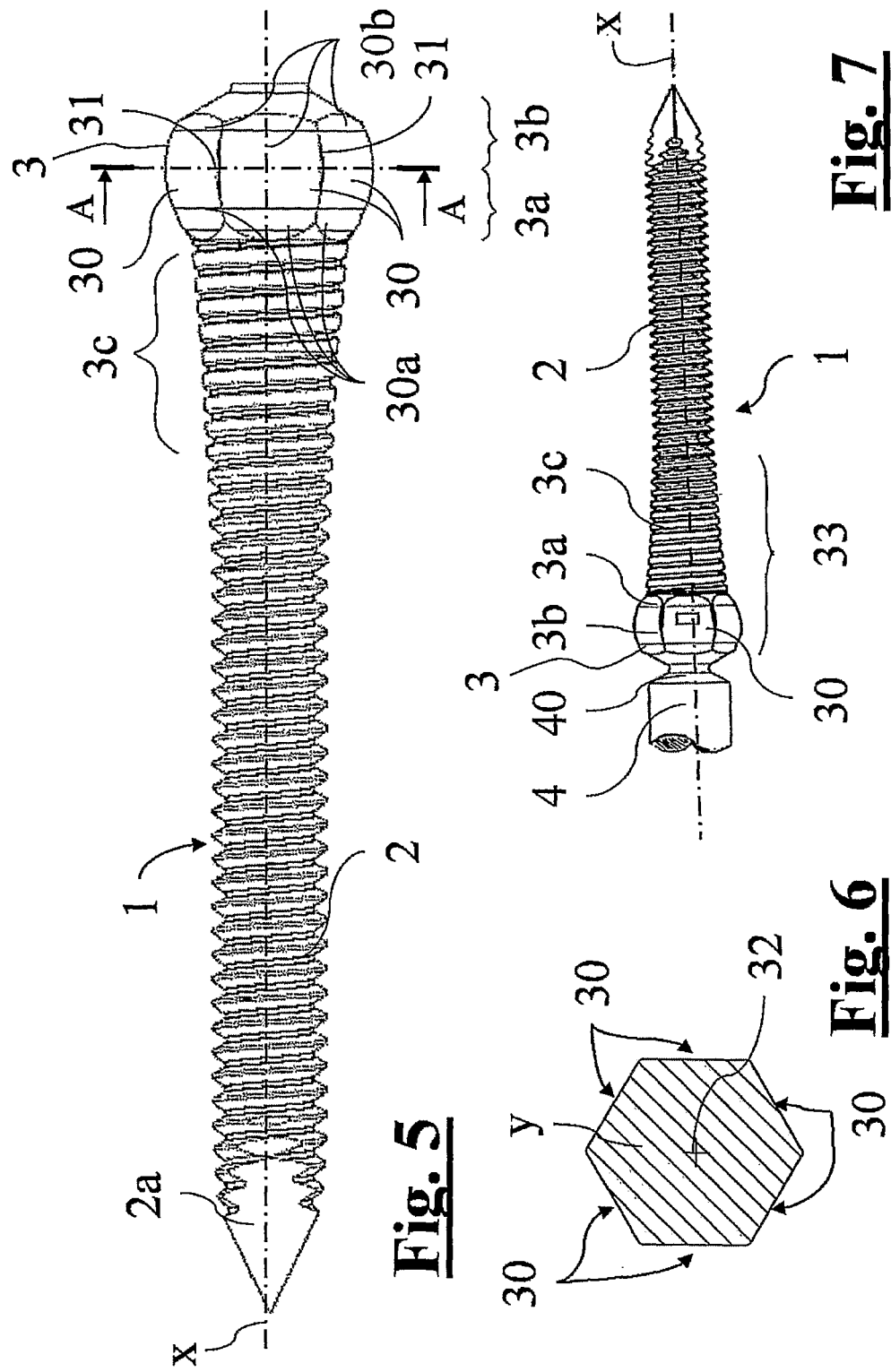

ENDOSSEOUS SCREWS AND ORTHOPAEDIC DEVICE TO ASSIST THE RIGID OSTEOSYNTHESIS OF FRACTURES

CROSS-REFERENCE TO RELATED APPLICATIONS

This application is a §371 national stage of PCT/IB2009/007856, filed Dec. 22, 2009, which claims priority to Italian Patent Application No. BO2008A000769, filed Dec. 23, 2008, the entirety of which are hereby incorporated by reference.

TECHNICAL FIELD

The present invention refers to an orthopedic device for the osteosynthesis of fractures, of the type comprising a plate and endosseous screws for fixing the same to a bone site.

The invention also refers to an endosseous screw for fixing a plate to a bone site

PRIOR ART

In order to facilitate correct osteosynthesis of bone fractures following surgical reduction, it is a known practice to use orthopedic devices comprising plates fixed to the fractured site by means of a plurality of endosseous screws.

Such screws, normally of the self-tapping and self-perforating type, may be adapted for engaging a support plate of the type called "with angular stability" by means of their cylindrical or conical threaded distal portion; this solution avoids angular micro-movements of the screw with respect to the plate, so that plate and engaged screws become a rigid, essentially monolithic body which is rigidly associated to the bone site.

Endosseous screws, in order to allow their tightening on plate during surgical application, have known insertion means located at their respective heads. In particular, such insertion means may comprise a recessed hexagonal cavity for inserting an instrument, or a stem that may be engaged by the mandrel of a drill during tightening and successively removed by breaking.

Although being advantageous from various points of view, endosseous screws according to the known art have a serious drawback in that they are difficult to remove after complete osteosynthesis (screws with hexagonal recessed cavity), if not impossible to remove (shaft screws).

In fact, whereas shaft screws are totally lacking extraction means once the shaft has been removed, recessed screws may be untightened by inserting the instrument in the same cavity provided for tightening. Moreover, the recessed hexagonal cavity allows the advantageous use of instruments with suitably shaped heads, which allow untightening of screws even in the absence of a perfect alignment between screw head and instrument head.

But unfortunately, in practice, the extraction hexagonal recessed screws is rarely without complications. In fact, during osteosynthesis or surgical removal the screw cavity is often occluded or deformed. In situation such as these the untightening operation is very complicated, or even impossible.

The drawback described above is particularly critical precisely in the case of angular stability plates; the engagement between screws and holes in the plate effectively complicates their extraction.

The technical problem to be solved by the present invention is therefore to provide an orthopedic device of the abovementioned type, having a structure that allows an easy removal of the screws from the plates after osteosynthesis.

SUMMARY OF THE INVENTION

Based on the following solution of the abovementioned technical problem, the present invention consists in an endosseous screw according to claim 1, and also in an orthopedic device according to claim 12.

The idea for solving the technical problem is based on the provision of screws used for fastening the plate to the bone, having an external profile accessible from the outside by means of cutaneous incision, to allow a tubular manipulating wrench to be inserted.

Essentially, the screw head has facets that define an external peripheral profile suitable for engagement by a tubular manipulating wrench, to allow the extraction of the screw from a bone site in which it has been inserted.

More in particular, the screw head may be easily inserted into the manipulating wrench, even at an angle, always allowing the transmission of torque between wrench and screw, thus facilitating the removal of the orthopedic device.

Further characteristics and advantages of the orthopedic device according to the invention will become evident by means of the following detailed description of one of its embodiments, in a non-exclusive way, with reference to the appended figures supplied by way of non-limiting example.

BRIEF DESCRIPTION OF THE DRAWINGS

FIG. 3 shows a lateral view of a partial section of the device of FIG. 1 during the extraction phase of endosseous screws inserted in the same;

FIG. 4 shows a lateral view of a greatly magnified detail of the device in FIG. 3;

FIG. 5 shows a lateral view of an endosseous screw according to the present invention;

FIG. 6 shows a sectional view along line A-A of the screw of FIG. 5;

FIG. 7 shows a lateral view of an endosseous screw according to the invention in a different embodiment.

DETAILED DESCRIPTION

With reference to the appended figures, and in particular to FIGS. 1-4, the number of reference 10 generally indicates an orthopedic device for rigid osteosynthesis of fractures, of the type comprising a plate 102 with at least a through hole 103 and at least one endosseous screw 1 provided for insertion into said hole.

Figure 2:
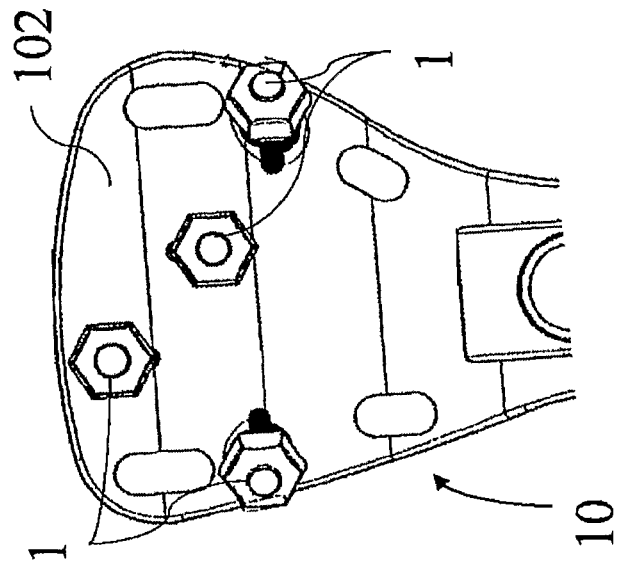
FIG. 2 shows a front view of device of FIG. 1.
Figure 1:
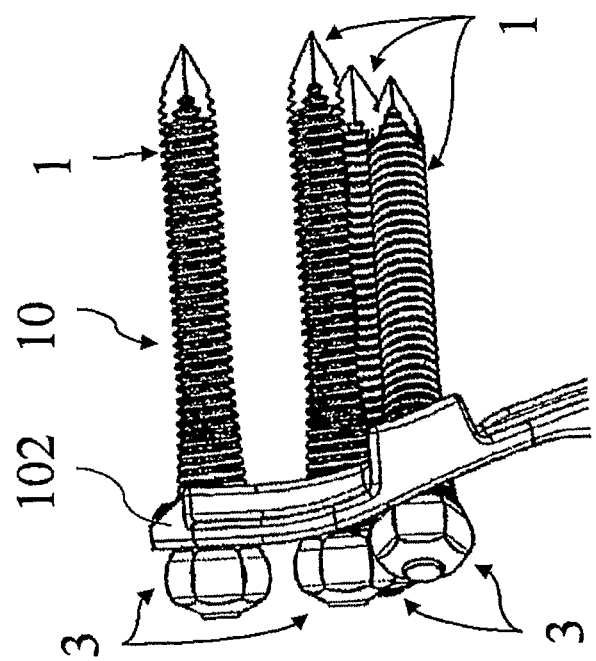
FIG. 1 shows a lateral view of an orthopedic device for the rigid synthesis of fractures, according to the present invention.

There is preferably more than one endosseous screw 1, four in the example shown in FIGS. 1 and 2.

The endosseous screw 1 according to the invention comprises a shaft 2, which is at least partially threaded, insertion means for inserting the screw into a bone site 300 and a distal portion of screw, which is provided for engaging the plate 102 in order to fasten the same to the bone site 300.

In particular, the distal portion 33 of the screw comprises a screw head 3 and a longitudinally extended portion.

The head 3 has facets 30 which define an external peripheral profile which may engage with a tubular manipulating wrench 101, to allow the screw 1 to be extracted from the bone site 300 where it has been inserted.

Moreover, the same facets 30 may also constitute the abovementioned insertion means. In fact, the manipulating wrench 101 of the type used for removal of screws may be applied by associating the same to the facets 30, for insertion of said screws 1 into the bone site 300.

The insertion means of screw 1 may alternatively comprise, as in the embodiment of FIG. 7, a longitudinal stem 4 associated to head 3 of screw 1, for manipulating the screw during its insertion into the bone structure of a patient. In particular, the longitudinal stem 4 allows the screw 1 to be attached to the mandrel of a drill.

The endosseous screw 1 shown in FIG. 7 also comprises an annular weakening groove 40 interposed between the longitudinal stem 4 and the head 3, to facilitate the separation by breaking off the longitudinal stem 4 after the insertion of screw 1. The breaking at the annular groove 40 is obtained by applying a predefined torque, in accordance with the size of the groove, to the longitudinal stem 4 after implant of screw 1.

It is to be noted that in this embodiment the facets 30 of head 3 are only used for untightening the screw, and therefore do not represent insertion means but only extraction means.

According to the present invention, in order to allow the engagement of the manipulating wrench 101 even under angled orientations with respect to a longitudinal axis x of the endosseous screw 1, the external peripheral profile of the head 3 is shaped like a barrel.

In this case, the term "barrel" indicates in a wholly general sense a solid body laterally delimited by a convex surface extending between two opposed edges. Therefore such a solid body has a median section with a surface that is greater than the one delimited by the two opposite edges.

As a result of the morphological properties described above, as is clearly shown in appended FIGS. 3 and 4, the head 3 can easily be inserted into the manipulating wrench 101, even if the latter is angled with respect to the longitudinal axis x of the screw 1, in any case allowing the transmission of torque between the wrench and the screw, thereby facilitating the removal of the device 10.

The longitudinal portion is composed of a threaded conical portion 3c that connects the shaft 2 and the head 3. This threaded conical portion 3c is provided for threadedly engaging hole 103 of plate 102, providing angular stabilization of the orthopedic device 10.

Preferably, the threaded conical portion 3c—being part of the distal portion 33 of the screw—has a thread of a triangular cross-section, whereas the shaft 2 has a conically slotted thread. Both threads are continuous without interruption of the threading.

Preferably, the shaft 2 of the endosseous screw 1 is entirely threaded and provided with an auto-perforating point 2a, which interacts with the abovementioned insertion means, to allow for the perforation of the bone site where the endosseous screw 1 has been inserted.

As already said, the facets 30 define an external barrel-shaped peripheral profile to allow for engagement with the head of the tubular manipulating wrench 101 even if the latter is inclined with respect to the longitudinal axis x of screw 1. In this case, the direction of the wrench head is defined by the rotational axis of the instrument when manipulated.

To this end, the facets 30 are not parallel to the longitudinal axis x of screw 1, but rather curvilinear and convex.

The head 3 has a median transversal section A-A, i.e. positioned on a plane perpendicular to the longitudinal axis x, with a profile suitable for engaging a corresponding profile of head of the manipulating wrench 101 when the wrench is aligned with the longitudinal axis x of screw 1. Preferably, the profile of the head 3 along the median section A-A is defined by a regular polygon having an even number of sides; for example, a regular hexagon as in the embodiment illustrated in FIG. 6 (where six facets 30 are provided).

Median section A-A divides the head 3 in an internal portion 3a, which is positioned on the side of the conically threaded portion 3c, and an opposed external part 3b.

Each facet 30 may be subdivided into two portions 30a, 30b, respectively internal and external, that mirror each other divided in two by the median section A-A.

Each external portion 30b of a specific facet 30 of the head 3 corresponds to a respective internal portion 30a of another opposed facet with respect to said specific facet, so that at least a segment normal to both portions 30a, 30b exists, whose length is equal to the distance between the corresponding opposite facets 30, measured along median section A-A.

Due to this specific geometric property, the screw head 3 may be engaged between two parallel and opposed surfaces (which are for example defined by the hollow profile of a tubular manipulating wrench), independent from the inclination of the manipulating wrench with respect to axis x of screw 1. Therefore, the untightening may take place not only when the manipulating wrench is parallel to axis x, but also in case of relative inclination within a predetermined angle.

In the preferred embodiment, both portions 30a, 30b of the same facet 30 are not separated by an edge.

The facets 30 are identical, and are separated by a curvilinear edge 31.

Preferably, each facet 30 is symmetrical with respect to a plane perpendicular to the longitudinal axis x of screw 1 (in this particular case, with respect to a plane comprising median section A-A) and is defined by a portion of the surface of a cylinder having an axis which is perpendicular to the longitudinal axis x of screw 1.

The radius of the cylinder defining facets 30 is preferably greater than the apothem of the regular polygon defining the shaped profile along median section A-A.

The head 3 according to the invention, having the morphology described above, has a notable geometric property. First of all it is to be noted that screw 1, when the profile of the head 3 along the median section A-A is defined by a regular polygon with an even number of sides, has a plurality of planes with a transversal symmetry. In other words, all planes passing through the longitudinal axis x and one of the symmetry axes of the polygonal profile along the median section A-A are symmetry planes. In the example shown of a hexagonal profile, there are three symmetry planes.

Let us now conventionally define the center 32 of head 3 as the intersection between the median section A-A and the longitudinal axis x of the endosseous screw. It is to be noted that the set of facets 30 of the screw in the illustrated embodiments evolves according to a central symmetry with respect to said center 32.

Finally it is to be noted that, due to the use of opposed cylindrical surfaces to define the facets 30, the profile of head 3 with respect to any section passing through the center 32 and perpendicular to one of the transversal symmetry planes remains equal to the abovementioned polygonal section, which is defined with respect to median section A-A.

In the end, by using a common tubular manipulating wrench, on the condition that the instrument is oriented according to one of the symmetry planes defined above, it is possible to vary the angle between the head of the wrench 101 and the screw 1 all the while maintaining a form coupling between the two elements, so as to allow the untightening operation. An example of non-aligned coupling between the head of the wrench 101 and screw 1 during removal of the orthopedic device 10 is shown in FIGS. 3 and 4.

An advantage of screw 1 according to the invention derives from the possibility of always ensuring the engagement between the head of the screw and the manipulating wrench, independently from the orientation of the latter, due to the particular configuration of the external peripheral profile used.

As stated above, such an innovation allows the cutaneous incision for the removal of device to be limited, advantageously reducing surgical trauma.

Another advantage of the invention is due to the head portion protruding from the plate, which is of reduced size and without sharp edges, therefore avoiding the impingement phenomena.

Another advantage of the invention refers to the easy retrieval of head which is partially protruding from the plate surface.

A further advantage of the device according to the invention is the easier extraction of the screw due to the presence of the conical portion.

Obviously, in order to comply with specific and contingent needs a person skilled in the art may introduce various modifications and changes to the described endosseous screw and orthopedic device, which are all within the scope of protection of the invention, as defined in the following claims.

The invention claimed is:

1. An endosseous screw for fixing a plate to a bone site, comprising:
    a shaft at least partially threaded,
    means to insert the screw into a bone site, and
    a distal portion provided for engaging the plate to fasten it to the bone site, said distal portion comprising a head and a conical threaded portion, the conical threaded portion being adjacent to the shaft and suitable for threadedly engaging a hole of the plate,
    wherein the head comprises curvilinear facets defining an external peripheral profile having a convex barrel-like shape,
    wherein the facets are even in number and define a regular polygonal section along a median section of the head, said median section being a section positioned on a plane perpendicular to the longitudinal axis of the screw and dividing each facet into two identical curvilinear portions which mirror each other with respect to the median section, said portions of each facet defining the external peripheral profile of the head of the screw, and
    wherein the distal portion is configured in such a manner that when the conical threaded portion engages the hole of the plate, the head in its entirety projects externally from the plate, so that the facets remain exposed in order to allow a stable coupling with a tubular manipulating wrench, the stable coupling being maintained during an untightening phase of the screw from the plate, even when the tubular manipulating wrench is oriented in an inclined direction with respect to a longitudinal axis of the endosseous screw.

2. The endosseous screw according to claim 1, wherein the distance between two opposite portions of two opposite facets on the opposite parts of the median section is equal to the distance between the respective opposite facets measured along the median section.

3. The endosseous screw according to claim 2, wherein each facet is symmetrical with respect to a plane perpendicular to the longitudinal axis of the screw and is defined by a portion of the surface of a cylinder having an axis perpendicularly intersecting said longitudinal axis.

4. The endosseous screw according to claim 3, wherein a radius of the cylinder defining the facets is preferably greater than a apothem of a regular polygon defining the shaped profile along the median section.

5. The endosseous screw according to claim 1, wherein the facets are all identical, and are separated by a curvilinear edge.

6. The endosseous screw according to claim 1, wherein the conical threaded portion has a thread with a triangular section, the shaft having a thread with a slotted conical section.

7. The endosseous screw according to claim 1, wherein the means to insert the screw comprise a longitudinal stem associated with the head of the screw, for manipulating the screw during the insertion phase of the same, and an annular weakening groove interposed between said longitudinal stem and the head, said groove being such as to allow the separation by breaking off the longitudinal stem after insertion of screw.

8. The endosseous screw according to claim 1, wherein the shaft of the endosseous screw is completely threaded and has an auto-perforating point.

9. An orthopedic device for the osteosynthesis of fractures, comprising:
    a plate with at least a through hole, and
    at least one endosseous screw for fixing the plate to a bone site,
    said endosseous screw comprising a shaft at least partially threaded,
    means to insert the screw into the bone site and
    a distal portion provided for engaging said plate to fasten it to said bone site said distal portion comprising a head and a conical threaded portion, the conical threaded portion being adjacent to the shaft and suitable for threadedly engaging a hole of the plate,
    wherein the head comprises curvilinear facets defining an external peripheral profile having a convex barrel-like shape,
    wherein the facets of the head of the screw are even in number and define a regular polygonal section along a median section of the head, said median section being a median transversal section positioned on a plane perpendicular to the longitudinal axis of the screw and dividing each facet of the head of the screw into two curvilinear portions which mirror each other with respect to the median transversal section, said portions of each facet defining the external peripheral profile of the head of the screw, and
    wherein the head of the screw in its entirety projects externally from the plate when the conical threaded portion engages the hole of the plate, so that the facets remain exposed in order to allow a stable coupling with a tubular manipulating wrench, the stable coupling being maintained during an untightening phase of the screw from the plate, even when the tubular manipulating wrench is oriented in an inclined direction with respect to a longitudinal axis of the endosseous screw.

10. A system for fixing and extracting an endosseous screw from an orthopedic device for the osteosynthesis of fractures, comprising:
    an orthopedic device for the osteosynthesis of fractures comprising a plate with at least a through hole and at least one endosseous screw for fixing the plate to a bone site,
    said endosseous screw comprises a shaft at least partially threaded,
    means to insert the screw into the bone site, and
    a distal portion provided for engaging said plate to fasten it to said bone site, said distal portion comprising a head and a conical threaded portion, the conical threaded portion being adjacent to the shaft and suitable for threadedly engaging a hole of the plate, wherein the head comprises curvilinear facets defining an external peripheral profile having a convex barrel-like shape, wherein the facets of the head of the screw are even in number and define a regular polygonal section along a median section of the head, said median section being a median transversal section positioned on a plane perpendicular to the longitudinal axis of the screw and dividing each facet of the head of the screw into two curvilinear portions which mirror each other with respect to the median transversal section, said portions of each facet defining the external peripheral profile of the head of the screw, and a tubular manipulating wrench for engaging the external peripheral profile of head of the screw, and wherein the conical threaded portion is configured to engage the hole of the plate in such a manner that the head of the screw in its entirety projects externally from the plate, so that the facets remain exposed in order to allow a stable coupling with a tubular manipulating wrench, the stable coupling being maintained during an untightening phase of the screw from the plate, even when the tubular manipulating wrench is oriented in an inclined direction with respect to a longitudinal axis of the endosseous screw.

* * * * *